US006894052B1

(12) United States Patent
Leonardi et al.

(10) Patent No.: US 6,894,052 B1
(45) Date of Patent: May 17, 2005

(54) DIARYLALKYLPIPERAZINES ACTIVE ON THE LOWER URINARY TRACT

(75) Inventors: Amedeo Leonardi, Milan (IT); Gianni Motta, Barlassina (IT); Carlo Riva, Varese (IT); Rodolfo Testa, Vignate (IT)

(73) Assignee: Recordati S.A. Chemical and Pharmaceutical Company, Chiasso (CH)

( * ) Notice: Subject to any disclaimer, the term of this patent is extended or adjusted under 35 U.S.C. 154(b) by 0 days.

(21) Appl. No.: 09/127,059

(22) Filed: Jul. 31, 1998

Related U.S. Application Data

(60) Provisional application No. 60/070,269, filed on Dec. 31, 1997.

(30) Foreign Application Priority Data

Aug. 1, 1997 (IT) ........................................ MI97A1861

(51) Int. Cl.⁷ .................. A61K 31/496; C07D 295/096; C07D 295/073; C07D 401/14; C07D 403/14
(52) U.S. Cl. ............................ 514/253.01; 514/253.09; 514/254.09; 514/254.11; 514/255.03; 544/360; 544/364; 544/373; 544/377; 544/393; 544/394
(58) Field of Search .............................. 544/392, 393, 544/394, 373, 377, 360, 364; 514/253.09, 253.01, 254.09, 254.11, 255.03, 252, 254

(56) References Cited

U.S. PATENT DOCUMENTS

| | | | |
|---|---|---|---|
| 3,030,367 A | 4/1962 | Jansen et al. | 544/392 |
| 3,230,256 A * | 1/1966 | Van der Stelt et al | 260/566 |
| 3,435,036 A | 3/1969 | Regnier et al. | |
| 3,457,263 A | 7/1969 | Regnier et al. | |
| 3,472,854 A | 10/1969 | Archer | 544/370 |
| 4,017,624 A | 4/1977 | Maruyama et al. | |
| 4,060,526 A | 11/1977 | Shetty | |
| 4,092,416 A | 5/1978 | Winter et al. | 514/253 |
| 4,206,213 A * | 6/1980 | Kleeman et al. | 544/379 |
| 5,177,078 A * | 1/1993 | Ward et al. | 514/253 |
| 5,532,242 A | 7/1996 | Cliffe et al. | |
| 5,723,464 A | 3/1998 | Brightwell et al. | |
| 5,773,469 A | 6/1998 | Kanojia et al. | |
| 5,807,856 A | 9/1998 | Bock | |
| 5,990,114 A | 11/1999 | Leonardi et al. | |
| 6,060,038 A | 5/2000 | Burns | |
| 6,071,920 A | 6/2000 | Leonardi | |
| 6,127,357 A | 10/2000 | Cliffe et al. | |
| 6,686,353 B1 * | 2/2004 | Shiota et al. | 514/218 |

FOREIGN PATENT DOCUMENTS

| | | |
|---|---|---|
| DE | 25 55 290 | 6/1977 |
| DE | 28 00 535 | 7/1978 |
| EP | 0 416 841 | 3/1991 |
| EP | 0 679 642 | 4/1995 |
| EP | 0 711 757 | 5/1996 |
| EP | 0 479 546 | 10/1996 |
| EP | 839 146 | 9/2000 |
| FR | 1 505 109 | 12/1967 |
| GB | 2 295 387 | 5/1996 |
| WO | WO 93/15062 | 8/1993 |
| WO | 95/04049 | 2/1995 |
| WO | 96/05817 | 2/1996 |
| WO | 97/43271 | 11/1997 |
| WO | 97/44329 | 11/1997 |
| WO | 99/06383 | 2/1999 |
| WO | 99/52875 | 10/1999 |

OTHER PUBLICATIONS

Grant & Hackh's Chemical Dictionary (5th Ed.), p. 14 and 30. 1987.*
Hagan et al, European Journal of Pharmacology, 331, p. 169–174 (Jul. 23, 1997).*
Plilai et al, Indian J. Chem. 14 B, p. 714–716 (1976).*
Patel et al Indian J. Exp. Biol., vol. 9, Jan. 1971, 117–119.
Ananthanarayanan et al., Indian J. of Chem., 12:31–37, Jan. 1974.
Regnier et al., Chimie Therapeutique, May–Jun. 1972, No. 3, 192–205 (English language summary included).
Regnier et al., J. Medicinal Chemistry, 1972, vol. 15, No. 3, 295–301.
Vadodaria, et al., Synthesis and Central Nervous System Depressant Activity of New Piperazine Derivatives and Related Compounds, vol. 12, 860–865.
Mokrosz et al., Arch. Pharm., 328:604(1995).
Barron et al., J. Med. Chem. 8:836–841, 1965.
Abbott, et al., Heterocycles, 40:757, (1995).
Albertson, Org. React. 12, 205–218, (1962).
Andersson, Drugs of Today, 24:337–348, (1988).
Andersson, Drugs 35:477, (1988).
Baldwin et al., J. Org. Chem., 47:1386, (1982).
Bliss, C.I., Quart. J. Pharm. Pharmacolo. 11, 192–216, (1938).
Cheng et al., Biochem Pharmacol., 22:3099–3108, 1973.
C, Stockmeier et al. J. Life Sci. 38, 117–127, (1983).
Cramer et al., J. Org. Chem., 40:2267, (1975).
De Groat, Neurobiology of Incontinence, Ciba Foundation Symposium 151:27, (1990).
DeLean et al., Am. J. Physiol., 235:E97–E102, (1978).
Doherty, et al., J. Med. Chem 35, 2, (1992).
Dray, J. Pharmacol. Methods 13: 157, (1985).
Fargin, et al., Nature 335, 358–360, (1988).
Furstner, Synthesis, 571, (1989).
Greene, T.W., Chapter 7, "Protective Groups in Organic Synthesis", John Wiley and Sons, New York, (1981).
Guarneri, et al., Drugs of Today 30:91, (1994).

(Continued)

Primary Examiner—Emily Bernhardt
(74) Attorney, Agent, or Firm—Darby & Darby

(57) ABSTRACT

Disclosed herein are novel compounds and methods for the treatment of disorders of the lower urinary tract. The novel compounds are diarylalkylpiperazine derivatives. The methods comprise the administration of the novel compounds of the invention, and other compounds that bind to 5HT$_{1A}$ receptors, for treating disorders of the lower urinary tract.

8 Claims, No Drawings

OTHER PUBLICATIONS

Guarneri, et al., *Pharmocol. Res., 27*:173(1993).
Ishihara, *Chem. Pharm. Bull. 39,* 3236, (1991).
Kleemann et al., Arzn. Forsch., 31:1178, (1981).
Klemm et al., J. Org. Chem., 23:344, (1958).
Lepor, *Urology, 42*:483, (1993).
Lindley , Tetrahedron, 40:1433, (1984).
Louie et al., J. Org. Chem., 62:1268, (1997).
Maggi, C.A. et al., Brain Res., *380*:83, (1986).
Maggi, C.A. et al., *J. Pharmacol. Exp. Ther., 230*:500, (1984).
Makosza, Tetrahedron Letter, 673, (1969).
March, Adv. Org. Chem., 4th Ed., 1212, (1992).
March , Adv. Org. Chem., 4th Ed., 887, (1992).
Marcoux et al., J. Org. Chem., 62:1568, (1997).
Maryanoff et al., Chem. Rev., 89:863, (1989).
McGuire, Campbell's Urology, 5th Ed., 616–638, (1986).
Norman et al., J. Med Chem., 39:469, (1996).
Panizzon, Helv. Chim. Acta., 27:1748, (1944).
Perrone et al., II Farmaco., 50:505, (1995).
Pfeiffer et al., Annalen, 581:149, (1953).
Rathke, Org. React., 22:423, (1975).
Ruffman, *Int. Med. Res. 16*:317, (1988).
Synlett, Note 12:328, (1996).
Vadodaria et al., J. Med Chem., 12:860, (1969).
Wolfe et al., J. Org. Chem., 62:1264, (1997).

* cited by examiner

DIARYLALKYLPIPERAZINES ACTIVE ON THE LOWER URINARY TRACT

This application claims priority under 35 U.S.C § 119 from U.S provisional patent application Ser. No. 60/070,269 filed Dec. 31, 1997, which is incorporated by reference herein in its entirety.

FIELD OF THE INVENTION

This invention relates to diarylalkylpiperazines, to pharmaceutical compositions containing them and to uses for such derivatives and compositions.

BACKGROUND OF THE INVENTION

In mammals, micturition (urination) is a complex process that requires the integrated actions of the bladder, its internal and external sphincters, the musculature of the pelvic floor, and neurological control over these muscles at three levels (in the bladder wall or sphincter itself, in the autonomic centers of the spinal cord, and in the central nervous system at the level of the pontine micturition center (PMC) in the brainstem (pons) under the control of cerebral cortex) (De Groat, *Neurobiology of Incontinence*, (Ciba Foundation Symposium 151:27, 1990). Micturition results from contraction of the detrusor muscle, which consists of interlacing smooth muscle fibers under parasympathetic autonomic control from the sacral spinal cord. A simple voiding reflex is formed by sensory nerves for pain, temperature, and distension that run from the bladder to the sacral cord. However, sensory tracts from the bladder also reach the PMC, resulting in the generation of nerve impulses that normally suppress the sacral spinal reflex arc controlling bladder emptying. Thus, normal micturition is initiated by voluntary suppression of cortical inhibition of the reflex arc and by relaxation of the muscles of the pelvic floor and the external sphincter. Finally, the detrusor muscle contracts and voiding occurs.

Abnormalities of lower urinary tract function, e.g., dysuria, incontinence, and enuresis, are common in the general population. Dysuria includes urinary frequency, nocturia, and urgency, and may be caused by cystitis, prostatitis or benign prostatic hypertrophy (BPH) (which affects about 70% of elderly males), or by neurological disorders. Incontinence syndromes include stress incontinence, urgency incontinence, and overflow incontinence. Enuresis refers to the involuntary passage of urine at night or during sleep.

Prior to the work of the present inventors, treatment of neuromuscular dysfunction of the lower urinary tract has involved administration of compounds that act directly on the bladder muscles, such as flavoxate, a spasmolytic drug (Ruffman, *J. Int.Med.Res.* 16:317, 1988) also active on the PMC (Guarneri et al., *Drugs of Today* 30:91, 1994), anticholinergic compounds such as oxybutynin (Andersson, *Drugs* 35:477, 1988), or "mixed action" drugs like imipramine (Andersson, *Drugs of Today* 24:337, 1988). The use of α1-adrenergic receptor antagonists for the treatment of BPH is also common but is based on a different mechanism of action. (Lepor, *Urology*, 42:483, 1993).

However, treatments that involve direct inhibition of the pelvic musculature (including the detrusor muscle) may have unwanted side effects such as incomplete voiding or accommodation paralysis, tachycardia and dry mouth (Andersson, *Drugs* 35:477, 1988) and drugs like imipramine may have relevant side effects, in particular on the cardiovascular system (orthostatic hypotension, ventricular arrhytmia) at the therapeutic doses. Thus, it would be preferable to utilize compounds that act via the peripheral or central nervous system to, for example, affect the sacral spinal reflex arc and/or the PMC inhibition pathways in a manner that restores normal functioning of the micturition mechanism.

Flavoxate, oxybutynin and imipramine are representative drugs from three different classes of compounds currently used in the therapy of urinary incontinence. These drugs have been tested in animal models where their activity has been confirmed.

The compounds of the invention, described below, have few structural characteristics in common with the above cited drugs, other than a basic nitrogen atom.

The compounds of the invention are more potent, relative to the above cited drugs, in pharmacological tests predictive of activity on the lower urinary tract, in particular for activity against neuromuscular disfunction of the lower urinary tract. The compounds of the invention are also potent and selective ligands for the 5-$HT_{1A}$ serotonergic receptor.

Other compounds which have been discovered by the present inventors to be useful in the methods of the present invention, e.g., treatment of disorders of the urinary tract, are disclosed in French Patent 1,505,109; EP 479,546; DE patent 2,800,535; *Arch. Pharmacie.* 328:604 (1995); *Arzn. Forsch.* 31:1178 (1981) and *J. Med. Chem.* 2:860 (1969), all of which are incorporated by reference.

SUMMARY OF THE INVENTION

In one aspect, the invention is directed to compounds of formula I:

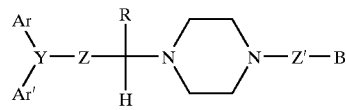

wherein each of Ar and Ar' is independently an optionally substituted aryl or heteroaryl group, Y is a nitrogen atom or a CH, C—OH, C—CN, C—CONH$_2$ group, R is a hydrogen atom or a lower alkyl group, B is an optionally substituted monocyclic or bicyclic aryl or heteroaryl group, Z is a methylene or an ethylene group, and Z' is a bond, a methylene or an ethylene group.

In another aspect, the invention is directed to compounds of formula I:

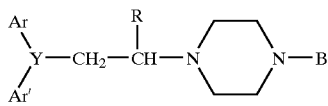

wherein
- each of Ar and Ar' is independently an optionally substituted aryl or heteroaryl group,
- Y is a nitrogen atom or a CH, C—OH, C—CN, C—CONH$_2$ group,
- R is a hydrogen atom or a lower alkyl group,
- B is a substituted aryl or optionally substituted heteroaryl group, with that provisos that:
  1) when any of Ar, Ar', or B is heteroaryl, any of nitrogen, oxygen, or sulfur can be present in the heteroaryl group only once;
  2) when any or both of Ar and Ar' are substituted, they cannot be substituted by a halogen atom; and
  3) when B is methoxyphenyl and Y is any of C—OH, C—CN, and C—CONH$_2$, then Ar and Ar' are not simultaneously unsubstituted phenyl or thienyl.

The invention also includes the enantiomers, diastereomers, N-oxides, crystalline forms, hydrates and pharmaceutically acceptable salts of these compounds, as well as metabolites of these compounds having the same type of activity (hereafter sometimes referred to as "active metabolites").

The invention further provides pharmaceutical compositions of a compound of formula I or an enantiomer, diastereomer, N-oxide, crystalline form, hydrate or pharmaceutically acceptable salt of the compound, in admixture with a pharmaceutically acceptable diluent or carrier.

In another aspect, the present invention is directed to methods for reducing the frequency of bladder contractions due to bladder distension by administering one or more selected compounds of Formula I to a mammal (including a human) in need of such treatment, in an amount or amounts effective for the particular use.

In a further aspect, the present invention is directed to methods for treating disorders of the urinary tract in a subject in need of such treatment, of administering an effective amount of a compound of Formula 1 to ameliorate at least one of urinary urgency, increased urinary frequency, incontinence, urine leakage, enuresis, dysuria, urinary hesitancy, and difficulty in emptying bladder.

In yet another aspect, the invention is directed to methods for binding to 5-HT$_{1A}$ serotonergic receptors, and, by virtue of this binding activity, to methods for the treatment of CNS disorders due to serotonergic dysfunction such as anxiety, depression, hypertension, sleep/wake cycle disorders, feeding behavior, sexual function and cognition disorders in mammals, particularly in humans, by delivering to the environment of the 5-HT$_{1A}$ serotonergic receptors, e.g., to the extracellular medium (or by administering to a mammal possessing such receptors) an effective amount of a compound of the invention.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

The activity of the compounds of the invention as inhibitors of frequency of micturition renders them useful for the treatment of neuromuscular dysfunctions of the lower urinary tract in mammals, including without limitation dysuria, incontinence and enuresis.

The structural features of the compounds of the invention render them significantly more potent than flavoxate and imipramine. The compounds of the invention are also more potent than oxybutynin, and also have a different, and superior, mode of action. The surprisingly superior properties of the compounds of the invention relative to the compounds of the prior art were determined by testing the prior art compounds and the compounds of the invention in a rat model. The rhythmic contraction of rat bladders was induced by filling the bladders with a physiologic solution. The effect of test compounds of the invention on the frequency and amplitude of the contractions was evaluated. Of particular interest is the time of disappearance of induced contractions of the bladder.

A comparison of the effects of currently available drugs (flavoxate, oxybutynin and imipramine) with the compounds of the invention in the above rat model are shown in Table 1. Compounds of the invention were longer-acting with respect to duration of induced bladder quiescence with no contractions than flavoxate, oxybutynin, and imipramine. In addition, in contrast to oxybutynin, the compounds of the invention did not affect the amplitude of the bladder contractions, suggesting no impairment of bladder contractility, and thus no impairment of bladder emptying when micturition is desired.

Finally, the demonstration that the compounds of the invention have a high affinity for the 5-HT$_{1A}$ receptor (Table 2) suggests a role for this receptor in the action of the compounds of the invention.

The pharmacological tests (and Tables) cited above are described in more detail in the Examples below.

As used herein, with regard to the scope of the variables Ar, Ar', and B, aryl radical means a mono or bicyclic aromatic radical having 6 to 12 carbon atoms (e.g. phenyl or naphthyl) which is optionally substituted by one or more substituents. Preferred substituents are alkyl, alkoxy, halogen, cyano, amido, acyl, nitro, amino, acylamino, alkylsulfonylamino, alkylamino substituents, except when specifically disclaimed. When B comprises an aryl group, two substituents on the aromatic ring may be connected together to form another ring system. For example, B may be a benzodioxanyl ring. Preferred groups at variable B are monocyclic aryl or bicyclic heteroaryl groups. Most preferred at B are an alkoxyphenyl or a bicyclie heteroaryl group containing one heteroatom.

The term heteroaryl group includes a mono or bicyclic aromatic group containing one or more heteroatoms (e.g. nitrogen, oxygen, sulfur) which contains 5 to 12 ring atoms. When it is specified that when any of Ar, Ar', or B is beteroaryl, any of nitrogen, oxygen, or sulfur can be present in the heteroaryl group only once, it means that the heteroaryl ring system will have only one occurrence of a given heteroatom. Thus, e.g., thiazolyl and isoxazolyl groups are not excluded from the scope of the claims by such a proviso, but, e.g., imidazolyl and pyrimidinyl groups would be excluded from the scope of claims with such a proviso.

It is preferred with regard to each Ar, that the variables be different. It is more preferred that one Ar be a phenyl group, and the other Ar be a pyridyl group. It is most preferred that one Ar is a substituted phenyl group and the other Ar is a 2-pyridyl group.

Preferred substituents at variable R are hydrogen and methyl. Preferred substituents at Y are C—CN and CH.

Subjects who can benefit from administration of the compounds and compositions of the invention include humans who are affected by neuromuscular dysfunction of the lower urinary tract, described by E. J. McGuire in "Campbell's UROLOGY" 5$^{th}$ Ed. 616–638, 1986, W.B. Saunders Company, and also include patients affected by any physiological dysfunction related to impairment of 5-HT$_{1A}$ receptor function. Such dysfunctions include, without limitation, central nervous system disorders such as depression, anxiety, eating disorders, sexual dysfunction, addiction, and related problems.

The present invention encompasses pharmaceutical formulations of the compounds disclosed above, as well as methods employing these formulations for treating neuromuscular dysfunction of the lower urinary tract such as dysuria, incontinence, enuresis, and the like. Dysuria includes urinary frequency, nocturia, urgency, and difficulty in emptying the bladder, i.e., a suboptimal volume of urine is expelled during micturition.

Incontinence syndromes include stress incontinence, urgency incontinence, and overflow incontinence. Enuresis refers to the involuntary passage of urine at night or during sleep.

Without wishing to be bound by theory, it is believed that administration of 5-HT$_{1A}$ receptor antagonists prevents unwanted activity of the sacral reflex arc and/or cortical mechanisms that control micturition. Thus it is contemplated that a wide range of neuromuscular dysfunctions of the lower urinary tract can be treated using the compounds of the present invention.

An "effective amount" of the compound for treating a urinary disorder is an amount that results in measurable amelioration of at least one symptom or parameter of the disorders described above.

An effective amount for treating the disorder can easily be determined by empirical methods known to those of ordinary skill in the art, such as by establishing a matrix of dosages and frequencies of administration and comparing a group of experimental units or subjects to each point in the matrix. The exact amount to be administered to a patient will vary depending on the state and severity of the disorder and the physical condition of the patient. A measurable amelioration of any symptom or parameter can be determined by a physician skilled in the art or reported by the patient to the physician. It will be understood that any clinically or statistically significant attenuation or amelioration of any symptom or parameter of urinary tract disorders is within the scope of the invention. Clinically significant attenuation or amelioration means perceptible to the patient and/or to the physician.

For example, a single patient may suffer from several symptoms of dysuria simultaneously, such as, for example, urgency and excessive frequency of urination, either or both of which may be reduced using the methods of the present invention. In the case of incontinence, any reduction in the frequency or volume of unwanted passage of urine is considered a beneficial effect of the present methods of treatment.

The compounds of the present invention may be formulated into liquid dosage forms with a physiologically acceptable carrier, such as, for example, phosphate buffered saline or deionized water. The pharmaceutical formulation may also contain excipients, including preservatives and stabilizers, that are well-known in the art. The compounds can be formulated into solid oral or non-oral dosage units such as, for example, tablets, capsules, powders, and suppositories, and may additionally include excipients, including without limitation lubricant(s), plasticizer(s), colorant(s), absorption enhancer(s), bactericide(s), and the like.

Modes of administration include oral and enteral, intravenous, intramuscular, subcutaneous, transdermal, transmucosal (including rectal and buccal), and by-inhalation routes. Preferably, an oral or transdermal route is used (i.e., via solid or liquid oral formulations, or skin patches, respectively).

The amount of the agent to be administered can range from between about 0.01 and about 25 mg/kg/day, preferably from between about 0.1 and about 10 mg/kg/day and most preferably from between about 0.2 and about 5 mg/kg/day. It will be understood that the pharmaceutical formulations of the present invention need not in themselves contain the entire amount of the agent that is effective in treating the disorder, as such effective amounts can be reached by administration of a plurality of doses of such pharmaceutical formulations.

In a preferred embodiment of the present invention, compounds are formulated in capsules or tablets, each preferably containing 50–200 mg of the compounds of the invention, and are most preferably administered to a patient at a total daily dose of 50–400 mg, preferably 150–250 mg, and most preferably about 200 mg for relief of urinary incontinence and dysfunctions amenable to treatment with 5-HT$_{1A}$ receptor antagonists.

The methods, Tables, and Examples described below are intended to more fully describe preferred embodiments of the invention and to demonstrate its advantages and applicability, without in any way limiting the scope of the invention.

SYNTHESIS OF THE COMPOUND OF THE INVENTION

Compounds of formula I according to the invention wherein Y is a CH group, R is H and Ar, Z, Z' and B have the same meanings as above can be prepared as shown by Scheme 1, below:

Scheme 1

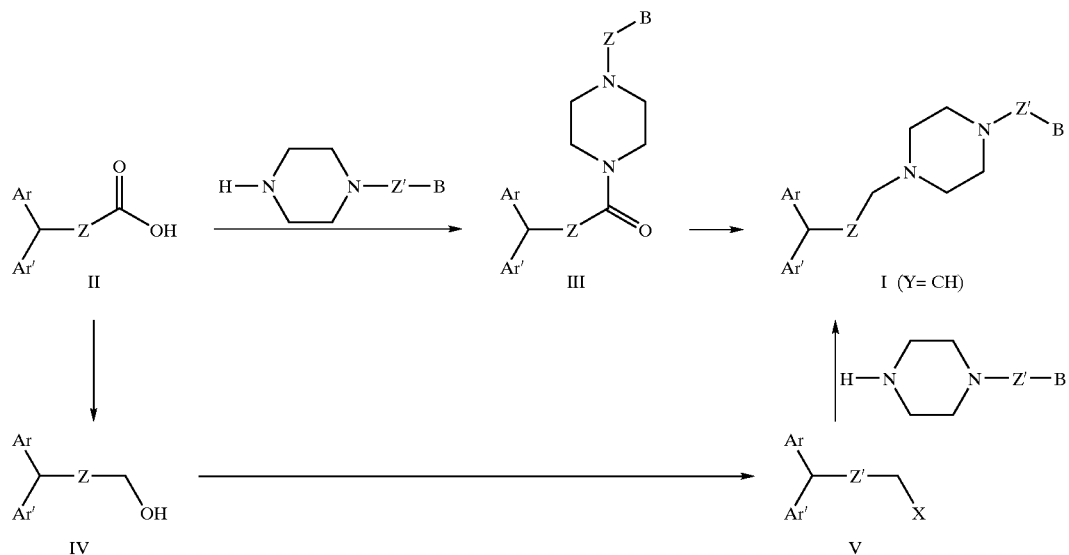

Intermediates of formula II are commercially available or their syntheses have been published in the literature and/or they can be prepared by conventional methods. In general, the intermediates of formula II can be synthesized, for example for compounds where Z is $CH_2$ from the corresponding diarylketones via a Reformatsky reaction with alkyl 2-bromoacetate and activated zinc (Org. React., 1975, 22, 423; Synthesis, 1989, 571) followed by hydrolysis, or by utilizing the Wadsworth-Emmons reaction with triethyl phosphonoacetate and a base (Chem. Rev., 1989, 89, 863), followed by hydrolysis. Additional synthetic routes to intermediates of formula II will be apparent to those skilled in the art.

Intermediates of formula II can be condensed with the appropriate N-monosubstituted piperazine derivative in the presence of a coupling agent (e.g. diethyl cyanophosphonate, dicyclohexylcarbodiimide or N,N'-carbonyldiimidazole) optionally in the presence of a promoting agent (e.g. N-hydroxysuccinimide, 4-dimethylaminopyridine) in an aprotic or a chlorinated solvent (e.g. N,N-dimethylformamide, chloroform, methylene chloride) at temperatures between about −20° C. and about 140° C. (Albertson, Org. React. 1962, 12, 205–218; Doherty et al., J. Med. Chem 1992, 35, 2; Staab et al., Newer Methods Prep. Org. Chem. 1968, 5, 61; Ishihara, Chem. Pharm. Bull. 1991, 39, 3236) to give compounds with formula III.

Other reaction procedures for achieving compounds of formula III include the mixed anhydride reaction, e.g., reaction of intermediates of formula II with an alkyl chloroformate in the presence of a tertiary amine (e.g. triethylamine) followed by addition of an appropriate piperazine reagent in an aprotic solvent (e.g. dioxane, methylene chloride), optionally in the presence of, e.g., 1-hydroxypiperidine as a promoting agent (Org. React. 1962, 12, 157). Other methods for the amidification of Intermediate II (or simple derivatives of II such as esters or acyl chlorides) with N-monosubstituted piperazines will be obvious to those skilled in the art. Yet another condensation method includes the reaction of a simple alkyl ester of II with an aluminum amide synthesized from piperazines and trimethylaluminum (J. Med. Chem 1996, 39, 4692).

Intermediates of formula III can be reduced to the desired compound I, where Y=CH, by the use of reducing agents capable of converting the amido functionality to an amino moiety. Such agents are, for example, lithium aluminum hydride or other complex aluminum hydrides. The reducing reactions are performed in diethyl ether or tetrahydrofuran, or in a stable diborane complex such as borane-tetrahydrofuran or borane-dimethyl sulfide or others (J. Org. Chem 1982, 47, 1389) used in an appropriate solvent (e.g. tetrahydrofuran). These boron compounds are particularly useful when the Ar group(s) are carrying reducible groups such as nitro; when diborane complexes are used, these reducible groups are not reduced. Many other useful reducing agents are known to those skilled in the art (March, Advanced Organic Chemistry, Wiley Interscience Ed., 1992, 1212).

An alternative reaction pathway to prepare the compounds of the invention where Y is CH is to reduce compounds of formula II using the reducing agents disclosed above or other conventional procedures (e.g., using $NaBH_4$ with $CaCl_2$, or by preparing and reducing mixed anhydrides, obtained by reaction of the carboxylic acid with a chloroformate, followed by treatment with $NaBH_4$) to alcohol compounds of formula IV. These alcohols are converted into the alkylating reagents V, where X is a leaving group (e.g., Cl, I, Br, p-toluenesulfonyloxy, methanesulfonyloxy), by conventional, well documented nucleophilic substitution procedures. Compounds of formula V can be reacted with monosubstituted piperazines affording compounds of formula I. These alkylation reactions are performed by conventional methods, well known to those skilled in the art. Usually the condensation is carried out in an aprotic (e.g. acetonitrile, dimethylformamide, toluene, dioxane, tetrahydrofuran) or protic solvent (e.g. ethanol, n-butanol).

If the reactants have a low melting point, the reaction can be carried out without any solvent. The substitution reactions can, optionally, be performed in the presence of a base (e.g. triethylamine, diisopropylethylamine, pyridine, 4-dimethylaminopyridine, potassium carbonate). Reaction temperatures are typically between room temperature and 180° C.

Compounds with formulas IV and V can also be prepared by alkylating an $ArCH_2Ar$ compound at its methane carbanion (obtained, e.g., by treatment of the $ArCH_2Ar$ compound with butyl lithium or another complex lithium or other alkali metal base) with compounds of formula $X-CH_2(CH_2)_nCH_2-OPrG$ or $X-CH_2(CH_2)_nCH_2-X$, respectively, zine compound with compounds of formulas $X-CH(R)-(CH_2)_n-CH_2-OPrG$ or $X-CH_2-(CH_2)_n-CH_2-X$, where X and n have the same meanings as above and PrG is a protecting group (e.g. O-tetrahydropyranyl) which can be easily removed after alkylation.

Compounds of formula I according to the invention where Y is a CH—CN or C—$CONH_2$ group and Ar, R, Z, Z' and B have the meanings set forth above can be prepared as shown by the Scheme 2, as follows:

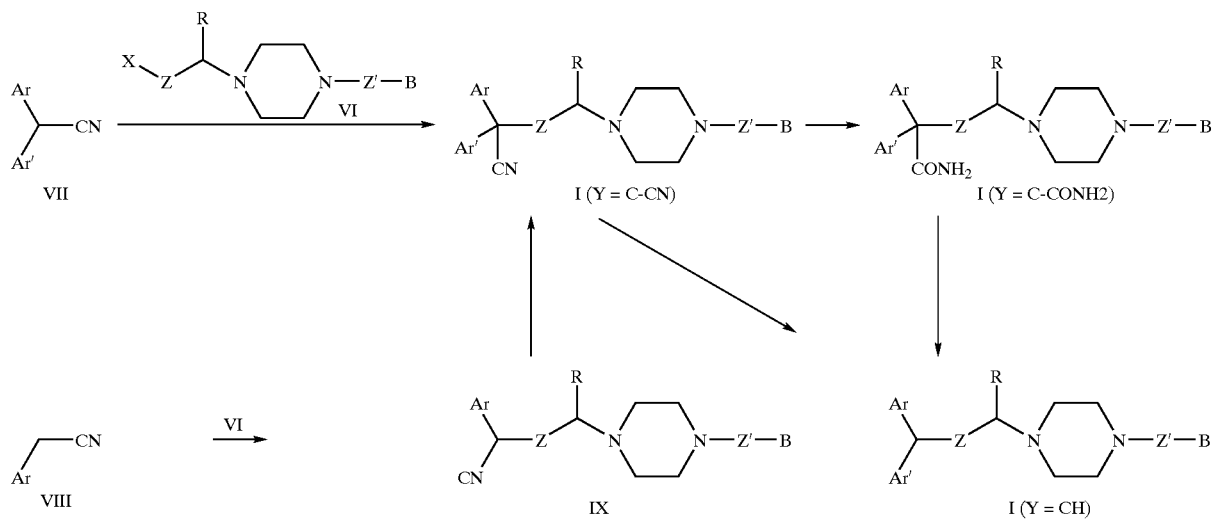

where X has the same meanings as above, n is 0 or 1 and PrG is a protecting group (e.g. O-tetrahydropyranyl) to be removed after alkylation.

Compounds of formula I can be directly prepared by reacting the carbanion $ArCH^-Ar$ obtained using alkali metal bases with compounds of formula VI, below, where X is a leaving group as described above:

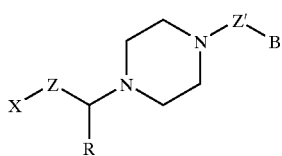

Compounds of formula VI can be conveniently prepared starting from compounds VI having a COOAlk group instead of the —$CH_2$—X terminal group. Conventional reduction procedures (e.g., treatment with lithium aluminum hydride or other metal complex hydrides) afford the corresponding compounds VI where X=OH. Conversion of hydroxyl groups to leaving groups (i.e., —OH to X) is a conventional procedure for those of ordinary skill. The starting esters can be prepared by well known Michael reactions or nucleophilic displacement reactions of a mono-substituted piperazine with a suitable 2,3-unsaturated ester or 2-haloester.

Alternative procedures to obtain compounds of formula VI consist of alkylating a suitable monosubstituted pipera- Intermediates of formula VII are generally commercially available or can be synthesized by conventional synthetic methods. Such intermediates can be converted into compounds with formula I, where X is C—CN, via alkylation of the corresponding carbanion with the suitable piperazine derivatives VI (*Il Farmaco*, 1995, 50, 505). The alkylation is performed by the use of an alkali metal base (e.g. butyl lithium, sodium amide, sodium hydride, lithium diisopropyl amide, lithium bis(trimethylsilyl)amide or other alkali metal bases known to those skilled in the art) in a proper aprotic solvent such as toluene, tetrahydrofuran, dimethoxyethane, dioxane, diglyme or other) at temperatures between −20° C. to the reflux temperature of the solvent. Compounds of formula I where X=C—CN can be easily converted by conventional procedures (partial hydrolysis by aqueous acid, e.g., 70% sulfuric acid or a Lewis acid at between room temperature and 80° C.; March, *Advanced Organic Chemistry*, Wiley Interscience Ed., 1992, 887) to compounds of formula I where X is C—$CONH_2$. Hydrolysis carried out under more severe conditions (e.g. 70% sulfuric acid at reflux) allows an alternative procedure to the method reported in the first reaction scheme affording compounds of formula I where X is CH.

Another route to the compounds of the invention consists of performing a carbon alkylation with a piperazine derivative of formula VI on $ArCH_2CN$ compounds of formula VIII, which are generally commercially available or accessible through conventional synthetic methods, to afford intermediates of formula IX. Compounds of formula IX can be arylated with an Ar—LG compound (where the leaving group LG represents a chlorine, bromine or fluorine atom). This typically can be carried out by a phase transfer reaction in the presence of a base (e.g. 50% sodium hydroxide; *Tetrahedron Letters*, 1969, 673) and a catalyst (e.g. triethylbenzyl ammonium chloride) in a suitable solvent (e.g. toluene) at between room temperature and the reflux temperature of the solvent. The aryl group should be activated to nucleophilic aromatic substitution by the presence of electron-withdrawing group(s) in the proper position or/and being an electron-deficient heterocycle (*Chem. Rev.*, 1951, 49, 273). Examples of such aryl groups are nitrosubstituted or halogen-substituted aryls.

Compounds of formula I of the invention where Y is a C—OH group and Ar, R Z, Z'and B have the same definitions as described above, can be prepared according to scheme 3, as follows:

Intermediates with formula XII can be converted to the corresponding azaanion, followed by N-alkylation of compounds of formula VI (see above). The alkylation is performed in the presence of a strong base (e.g. butyl lithium, sodium amide, sodium hydride, lithium diisopropyl amide, lithium bis(trimethylsilyl)amide or others well-known to those of ordinary skill in the art) in an aprotic solvent such as toluene, tetrahydrofuran, dimethoxyethane, dioxane, diglyme at temperatures from between −20° C. and the reflux temperature of the solvent.

Intermediates of formula XII are commercially available or may be prepared following the common procedures, e.g., by nucleophilic substitution of an Ar—NH₂ compound on a Ar—LG (where LG is a leaving group such as iodine, trifluoromethanesulfonyloxy, bromine, chlorine or fluorine). The nucleophilic substitution can be catalyzed and is typically performed in the presence of a base (e.g. sodium Scheme 3

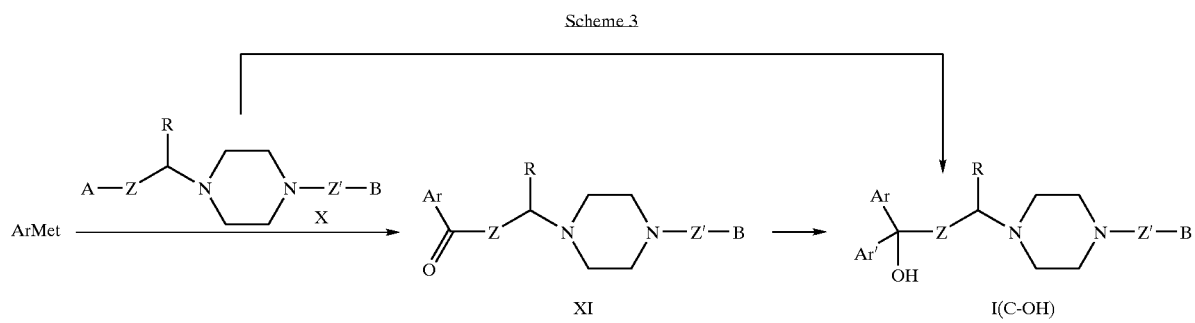

An aryl metal derivative ArMet where Met stands for metal (e.g. lithium or magnesium, prepared by reacting butyl lithium or magnesium turnings with an aryl bromide or an aryl iodide compound in tetrahydrofuran at between −70° C. and the solvent reflux temperature) is reacted in the same solvent at between −20° C. and the reflux temperature of the solvent with conventionally prepared derivatives of formula X, where A can represent a carboxylate. cyano, or CONH₂ group. X is preferably an alkyl piperazinopropionate or an alkyl piperazinoacetate. In some cases direct lithiation of the aryl species is feasible, e.g., in the case where an ortho dimethylaminocarbonyl or methoxy substituent is present on Ar. When A represents a (CH₃O)(CH₃)NC(O) group (i.e., a Weinreb amide), it is possible to perform a step by step reaction consisting of the isolation of ArC(O) intermediates with compounds of formula XI, followed by further reaction with another ArMet to afford the alcohol compounds of formula I, which also bear different Ar groups.

Compounds of the invention with formula I where Y is nitrogen may generally be prepared as shown by Scheme 4, as follows:

carbonate, lithium diisopropylamide, sodium tert-butoxide, etc.). Metal catalysts useful for nucleophilic substitution on aryl rings include, e.g., copper, copper (I) iodide or bromide or oxide (*Tetrahedron*, 1984, 40, 1433), nickel catalysts (*J. Org. Chem.*, 1975, 40, 2267) palladium dichloride, palladium diacetate, palladium tetrakis, bis(diphenylphosphine) palladium dichloride, palladium dibenzylidene acetone, bis (diphenylphosphinoferrocene)palladium dichloride (*Synlett*, 1996, 329; *J. Org. Chem.*, 1997, 62, 1568; 1997, 62, 1268; 1997, 62, 1264). Reactions can be performed at the melting temperature of the reactants, i.e., without solvent, or in a suitable solvent (e.g. dimethylacetamide, dimethylformamide, dioxane, toluene, tetrahydrofuran) at temperatures from room temperature to the reflux temperature of the solvent. The reactions can be facilitated by the use of a ligand (e.g. triphenyl phosphine or tri-o-tolylphosphine or bis(diphenylphosphino)ferrocene or 2,2'-bis (diphenylphosphino)-1,1'-binaphthyl or other commercially available phosphine ligands).

Scheme 4

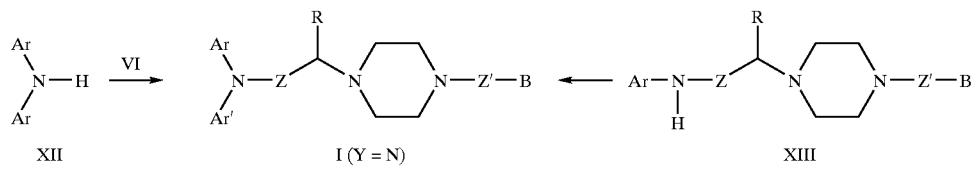

An alternative procedure to synthesize compounds of formula I, especially useful when one or both of the aryl groups bear nitro groups, consists in arylating amino intermediates of formula XIII by the same procedure described for the preparation of intermediates of formula XII, described above.

Intermediates with formula XIII are obtainable following conventional procedures well known to those skilled in the art, e.g., by alkylating an anilino derivative Ar—$NH_2$ with an appropriate compound of formula VI in a high boiling solvent (e.g. n-butanol) or at the melting temperature of the reactants. Alternatively, if the aryl moiety is sufficiently activated to be susceptible to nucleophilic aromatic substitution, compounds of formula XIII can be prepared by reacting an Ar—LG (where LG is defined as above) with an appropriate ω-aminoalkylpiperazine derivative. The reaction can be uncatalyzed and performed at the melting temperature of the reactants without solvent, or it can be done in a suitable solvent (e.g. n-butanol, dimethylformamide, dimethylacetamide) at temperatures between room temperature and the reflux temperature of the solvent. The reaction can also be catalyzed by a metal, as in the preparation of intermediates XII, described above.

When B is aryl or heteroaryl-lower alkylene, the above-described reaction procedures for the preparation of compounds of formula I can be employed, or, alternatively, the synthesis can be performed using piperazine derivatives where B is a protecting group (e.g. tert-butoxycarbonyl, benzyloxycarbonyl, benzyl or other amino protecting groups, described in Greene, "Protective Groups in Organic Synthesis", Wiley Interscience, New York, 1991). Applying the same general synthetic methods described above, compounds of formula I, where B is a protecting group, are obtained. Simple and conventional deprotection procedures allow the preparation of compounds with the formula XIV, below, which can be alkylated with an appropriate alkyl or heteroalkyl halide to afford compounds of the invention.

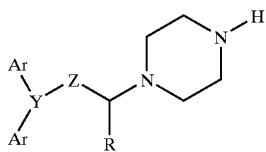

XIV

EXAMPLE 1

1-(3,3-diphenylpropyl)-4-(2-methoxyphenyl)piperazine hydrochloride a) 1-(3,3-diphenylpropionyl)-4-(2-methoxyphenyl)piperazine (Compound 1A):

To a solution of 1.13 g of 3,3-diphenylpropionic acid and 1.06 g of 1-(2-methoxyphenyl)piperazine in 25 mL of N,N-dimethylformamide at a temperature within the range of 0–5° C., were added, in succession, 0.9 mL of 93% diethyl cyanophosphonate and 0.77 mL of triethylamine under stirring. The resultant solution was then stirred at room temperature for 5 h, poured into 250 mL of water and extracted with ethyl acetate. The organic phase was then washed with water, dried on anhydrous sodium sulphate, and evaporated to dryness under vacuum. The obtained oily residue was then puirified by flash-chromatography (chloroform-ethyl acetate 9:1). This procedure afforded the title compound (100%).

$^1$H-NMR (CDCl$_3$, δ): 7.15–7.35 (m, 10H, phenyl protons); 6.75–7.05 (m, 4H, methoxyphenyl CHs); 4.69 (t, 1H, CH); 3.85 (s, 3H, OCH$_3$); 3.67–3.77 (m, 2H, (CH(H))$_2$NC(O)equatorial); 3.50–3.60 (m, 2H, (CH(H̲))$_2$NC(O)axial);3.09 (d, 2H, CH$_2$); 2.83–2.93 (m, 2H, piperazine protons); 2.67–2.77 (m, 2H, piperazine protons).

b) 1-(3,3-diphenylpropyl)-4-(2-methoxyphenyl)piperazine hydrochloride:

To a solution of 2.0 g of the compound described above, in Example 1A, in 45 mL of anhydrous tetrahydrofuran stirred at room temperature was added 0.44 g of lithium aluminum hydride. The obtained reaction mixture was then stirred at room temperature, for a period of 24 h, and then for 2.5 h at reflux. The mixture was then cooled, and 5 mL of ethyl acetate was added cautiously, followed by 5 mL of ethanol. Next, the mixture was poured into 225 mL of water, followed by extraction with ethyl acetate. The organic phase was washed with water, dried on anhydrous sodium sulphate, and then evaporated to dryness in vacuo. The crude product obtained by this means was then purified by flash chromatography (petroleum ether-ethyl acetate 7:3). The residue obtained from the evaporation of the recovered fractions was then dissolved in ethyl acetate, and to the resultant solution was added 1 molar equivalent of HCl (2 N solution, in ethanol). Filtration afforded 0.83 g (39%) of the title product.

$^1$H-NMR (CDCl$_3$, δ): 12.75–13.10 (br, 1H, NH$^+$); 7.15–7.35 (m, 10H, phenyl CHs); 6.80–7.12 (m, 4H, methoxyphenyl CHs); 3.99 (t, 1H, CH); 3.85 (s, 3H, OCH$_3$); 3.38–3.70 (m, 6H, piperazine protons, CH̲$_2$NH$^+$); 2.85–3.15 (m, 4H, piperazine protons); 2.65–2.82 (m, 2H, CH̲$_2$CH).

EXAMPLE 2

1-(3,3-diphenylpropyl)-4-[5-(2,3-dihydro-1,4-benzodioxinyl)]piperazine methanesulphonate a) 1-(3,3-diphenylpropionyl)-4-[5-(2,3-dihydro-1,4-benzodioxinyl)]-piperazine (Compound 2A):

This product was obtained in accordance with the method described above, (in Example 1a), with the sole difference that 1-(2-methoxyphenyl)piperazine was replaced here by 1-[5-(2,3-dihydro-1,4-benzodioxinyl)piperazine. The obtained crude product was purified by flash chromatography (chloroform-ethyl acetate 8:2). Yield: 85%.

$^1$H-NMR (CDCl$_3$, δ): 7.15–7.35 (m, 10H, phenyl CHs); 6.74 (dd, 1H, benzodioxane H7); 6.60 (dd, 1H, benzodioxane H6); 6.40 (dd, 1H, benzodioxane H8); 4.68 (t, 1H, CH); 4.15–4.35 (m, 4H, OCH$_2$CH$_2$O); 3.65–3.75 (m, 2H, (CH(H))$_2$NC(O)equatorial); 3.45–3.55 (m, 2H, (CH(H̲))$_2$NC(O)axial); 3.10 (d, 2H, CH$_2$C(O)); 2.85–2.95 (m, 2H, piperazine protons); 2.65–2.75 (m, 2H, piperazine protons).

b) 1-(3,3-diphenylpropyl)-4-[5-(2,3-dihydro-1,4-benzodioxinyl)]piperazine methanesulphonate:

This product was obtained in accordance with the method described above, (in Example 1b), with the sole exception that compound 2A was employed in place of compound 1A. The residue from column chromatography was dissolved in ethyl acetate, followed by the addition of one molar equivalent of methanesulphonic acid (0.5 M solution, in ethyl acetate). After maintaining the resultant solution overnight at 3° C., the crystallized title product was recovered by filtration. M.p.194–195° C. Yield: 21%.

$^1$H-NMR (DMSO-d$_6$, δ): 9.35–9.55 (br, 1H, NH$^+$); 7.12–7.40 (m, 10H, phenyl CHs); 6.75 (dd, 1H, benzodioxane H7); 6.50–6.58 (2dd, 2H, benzodioxane H6, H8); 4.18–4.28 (m, 4H, OCH$_2$CH$_2$O); 4.05 (t, 1H, CH); 3.45–3.68 (m, 4H, piperazine protons); 2.80–3.30 (m, 6H, piperazine protons, CHCH$_2$CH$_2$); 2.45–2.55 (m, 2H, CHCH$_2$CH$_2$); 2.30 (s, 3H, CH$_3$S).

EXAMPLE 3

3-[3,3-bis-(4-nitrophenyl)propyl]-4-(2-methoxyphenyl)piperazine dihydrochloride 0.8 H$_2$O a) 1-[3,3-bis-(4-nitrophenyl)propionyl]-4-(2-methoxyphenyl)-piperazine (Compound 3A):

This product was obtained in accordance with the method described above, (in Example 1a), with the sole exception that 3,3-diphenylpropionic acid was replaced here by 3,3-bis-(4-nitrophenyl)propionic acid (prepared in accordance with the method supplied by Pfeiffer et al., *Annalen* 1983, 581, 149). In addition, extraction was carried out here with chloroform rather than ethyl acetate. The obtained crude was purified by crystallization from 80% ethanol. The obtained solid (48%) melted at 159–163° C.

$^1$H-NMR (CDCl$_3$, δ): 8.18 (dd, 4H, nitrophenyl H3, 5); 7.42 (dd, 4H, nitrophenyl H2, 6); 6.80–7.14 (m, 4H, methoxyphenyl CHs); 4.97 (t, 1H, CH); 3.86 (s, 3H, OCH$_3$); 3.67–3.78 (m, 2H, CHCH$_2$); 3.58–3.67 (m, 2H, CON(CHH)$_2$ equatorials); 3.16 (d, 2H, CON(CHH)$_2$ axials); 2.90–3.07 (m, 4H, remaining piperazine protons).

b) 1-[3,3-bis-(4-nitrophenyl)propyl]-4-(2-methoxyphenyl) piperazine dihydrochloride.0.8 H$_2$O:

To a solution of 0.49 g of Compound 3A, in 6 mL of anhydrous tetrahydrofuran, stirred under a nitrogen atmosphere, was added, at a temperature of 0–5° C., 1.25 mL of borane-dimethyl sulfide (2 M solution, in tetrahydrofuran). The obtained mixture was then refluxed for 4 h, followed by cooling to 0° C. and by the addition of 1 mL of methanol, and, subsequently, 0.5 h of stirring within the temperature range 20–25° C. Afterwards, 0.5 ml of hydrochloric acid (4 N solution, in isopropanol) was added. The resultant mixture was then refluxed for 1 h, diluted with 20 mL of methanol, and evaporated to dryness in vacuo. The obtained residue was then taken up with 10 mL of water, and the resultant mixture was rendered basic by the addition of 1 N sodium hydroxide. This was followed by extraction with 3×5 mL of chloroform. The combined organic phases were then washed with water, dried over anhydrous sodium sulphate, and evaporated to dryness under vacuum. The residue was then dissolved in 18 mL methanol, followed by acidification of the obtained solution with excess 4 N hydrochloric acid in isopropanol. After 3 h at 0° C., the crystallized title product was recovered by filtration, affording 0.31 g (55.7%) of crystals melting at 191–194° C., and containing 0.8 mol of water.

$^1$H-NMR (CDCl$_3$, δ): 11.25–11.45 (br, 1H, NH$^+$); 8.20 (dd, 4H, nitrophenyl H3, 5); 7.70 (dd, 4H, nitrophenyl H2, 6); 6.85–7.07 (m, 4H, methoxyphenyl CHs); 5.85–6.18 (br, 2.6H, H$_2$O and NH$^+$); 4.54 (t, 1H, CH); 3.77 (s, 3H, OCH$_3$); 3.55–3.65 (m, 4H, piperazine protons); 3.07–3.25 (m, 4H, piperazine protons); 2.90–3.07 (m, 2H, CHCH$_2$CH$_2$N); 2.63–2.80 (m, 2H, CHCH$_2$CH$_2$N).

EXAMPLE 4

1-[3,3-bis-(4-methoxyphenyl)propyl]-4-(2-methoxyphenyl)piperazine dihydrochloride a) 1-[3,3-bis-(4-methoxyphenyl)propionyl]-4-(2-methoxyphenyl)piperazine dihydrochloride (Compound 4A):

This product was obtained in accordance with the method described above, (in Example 1a), with the sole exception that, in place of 3,3-diphenylpropionic acid, 3,3-bis-(4-methoxyphenyl)propionic acid (prepared in accordance with the method supplied by Klemm, L., in *J. Org. Chem.* 1958, 23, 344) was used here. In addition, the extraction was carried out here with diethyl ether, instead of ethyl acetate, and the obtained extract, following its drying on anhydrous sodium sulphate, was acidified with hydrochloric acid (3 N solution, in diethyl ether). The precipitate was then recovered by filtration and recrystallized from acetone. The title product (65.5%) melted at 175–179° C.

$^1$H-NMR (DMSO-d$_6$, δ): 9.50 (br, 1H, NH$^+$); 7.15–7.25 (m, 4H, AA' 4-methoxyphenyl CHs of the AA'BB' system); 6.88–7.25 (m, 4H, 2-methoxyphenyl CHs); 6.76–6.85 (m, 4H, BB' 4-methoxyphenyl CHs of the AA'BB' system); 4.38 (t, 1H, CH); 3.82 (s, 3H, OCH$_3$); 2.88–3.15 (m, 6H, piperazine protons, C(O)CH$_2$).

b) 1-[3,3-bis-(4-methoxyphenyl)propyl]-4-(2-methoxyphenyl)piperazine dihydrochloride:

This product was obtained in accordance with the procedure described above, (in Example 3b), with the sole exception that Compound 4A was employed here in place of Compound 3A. In addition, extraction was carried out here with ethyl acetate rather than chloroform. The obtained residue was dissolved in diethyl ether; then, after treatment with charcoal, the resultant solution was acidified with excess hydrochloric acid (3 N solution, in diethyl ether). After 3 h, the precipitate was recovered by filtration; the title product melted at 163–171° C.

$^1$H-NMR (DMSO-d$_6$, δ): 8.80–8.90 (br, 2H, NH$^+$); 7.18–7.30 (m, 4H, AA' 4-methoxyphenyl CHs of the AA'BB' system); 6.80–7.05 (m, 8H, 2-methoxyphenyl CHs and BB' 4-methoxyphenyl CHs of the AA'BB' system); 3.92 (t, 1H, CH); 3.78 (s, 3H, OCH$_3$); 3.71 (s, 6H, 2 OCH$_3$); 3.35–3.62 (m, 4H, piperazine protons); 3.03–3.25 (m, 4H, piperazine protons); 2.85–3.03 (m, 2H, CH$_2$CH$_2$CH); 2.42–2.52 (m, 2H, CH$_2$CH$_2$CH).

EXAMPLE 5

1-[N-N-bis-(2-pyridyl)-2-aminoethyl]-4-(2-methoxyphenyl)piperazine hydrochloride:

To a solution of 1.71 g of bis-(2-pyridyl)amine in 50 mL of toluene, under stirring at room temperature, was added 0.55 g of 95% sodium amide, followed by 2.54 g of 1-(2-chloroethyl)-4-(2-methoxyphenyl)piperazine. The obtained reaction mixture was then refluxed for 24 h, followed by cooling to room temperature and subsequent careful dilution with 10 mL of methanol. Afterwards, after 15 min of stirring, 20 mL of water and 20 mL of ethyl acetate were added. Then, after 10 min of further stirring, phase separation was carried out, and the aqueous phase was subsequently re-extracted with ethyl acetate. The combined organic phases were then washed with water, dried on sodium sulphate, and then evaporated to complete dryness under vacuum. The crude residue was then purified by flash chromatography (petroleum ether-ethyl acetate-2.2 N solution of ammonia in methanol; gradient from 6:4:0.2 to 4:6:0.2). The recovered fractions were then evaporated to complete dryness, yielding 2.51 g (64.5%) of the title product as a base. This material was subsequently dissolved in 45 mL of ethyl acetate, to which was added 1 molar equivalent of hydrochloric acid (1 M solution in ethanol). Overnight resting at 0° C. afforded the title product, in crystalline form, which melted at 218–220° C.

$^1$H-NMR (DMSO-$d_6$, δ): 8.40 (dd, 2H, pyridine H6); 7.74 (ddd, 2H, pyridine H4); 7.28 (dd, 2H, pyridine H3); 6.90–7.15 (m, 6H, pyridine H5, phenyl CHs); 4.58 (t, 2H, PyNCH$_2$); 4.35–5.15 (br, 1H, NH$^+$); 3.80 (s, 3H, OCH$_3$); 2.95–3.35 (m, 10H, piperazine protons and PyNCH$_2$C$\underline{H}_2$).

EXAMPLE 6

1-[3-cyano-3,3-bis-(2-pyridyl)propyl]-4-(2-methoxyphenyl)piperazine

To a suspension of 0.21 g of 95% sodium amide in 2 mL of 1,2-dimethoxyethane was added dropwise a solution of 0.78 g of 2,2-bis-(2-pyridyl)acetonitrile (prepared as described in *Heterocycles* 1995, 40, 757) in 8 mL of 1,2-dimethoxyethane, with stirring under a nitrogen atmosphere at room temperature. After 1 h, there were added dropwise, 1.02 g of 1-(2-chloroethyl)-4-(2-methoxy-phenyl)piperazine dissolved in 4 mL of 1,2-dimethoxyethane. The resultant reaction mixture was then refluxed for 20 h, followed by cooling to room temperature, and was then poured cautiously into 40 g of ice, diluted with water, and extracted with ethyl acetate. The combined organic phases were then washed with water, dried on sodium sulphate, and then evaporated thoroughly under vacuum. The obtained crude was then purified by flash chromatography (ethyl acetate-methanol gradient from 10:0 to 9:1). The recovered fractions were then evaporated to complete dryness, affording 1.13 g of the title product (68.4%).

$^1$H-NMR (CDCl$_3$, δ): 8.60 (dd, 2H, pyridine H6); 7.58–7.73 (m, 4H, pyridine H3, 4); 7.22 (ddd, 2H, pyridine H5); 6.83–7.03 (m, 4H, methoxyphenyl CHs); 3.84 (s, 3H, OCH$_3$); 2.85–3.08 (m, 6H, piperazine protons, CC$\underline{H}_2$CH$_2$N); 2.55–2.70 (m, 6H, piperazine protons, CCH$_2$C$\underline{H}_2$N).

EXAMPLE 7

1-[3-cyano-3-phenyl-3-(2-pyridyl)propyl]-4-(2-methoxyphenyl)piperazine dihydrochloride This product was prepared as described above, (in Example 6), with the sole exception that 2,2-bis-(2-pyridyl)acetonitrile was replaced here with 2-phenyl-2-(2-pyridyl)acetonitrile (prepared as described in *Helv. Chim. Acta* 1944, 27, 1748). The obtained crude was purified by flash chromatography (ethyl acetate-petroleum ether 6:4). After subsequent evaporation of the recovered fractions, this procedure afforded the title product as a base (86%). This product was subsequently dissolved in ethanol, to which was then added excess hydrochloric acid (5 M solution, in isopropanol). Finally, after overnight resting at room temperature, the title product was recovered by filtration and melted at 228–230° C.

$^1$H-NMR (CDCl$_3$, δ): 11.50–11.75 (br, 1H, NH$^+$); 8.65 (dd, 1H, pyridine H6); 8.25–8.60 (br, 1H, NH$^+$); 8.40 (ddd, 1H, pyridine H4); 7.45–7.60 (m, 7H, pyridine H3, 5, phenyl CHs); 6.85–7.10 (m, 4H, methoxyphenyl CHs); 3.77 (s, 3H, OCH$_3$); 3.00–3.75 (m, 12H, piperazine protons and CH$_2$CH$_2$).

EXAMPLE 8

1-[3,3-bis-(2-pyridyl)propyl]-4-(2-methoxyphenyl)piperazine

A mixture of 2.44 g of compound of Example 6 and 12 mL of 70% sulphuric acid was stirred for 1.5 h at 125° C. The obtained reaction mixture was then cooled to room temperature, followed by careful pouring into 100 g of ice, dilution with water, alkalinization with 35% sodium hydroxide, and extraction with ethyl acetate (3×40 mL). The combined organic phases were then washed with water, dried on anhydrous sodium sulphate, and then evaporated to complete dryness under vacuum. The obtained crude was then purified by flash chromatography (ethyl acetate-2.2 N solution of ammonia in methanol 9.6:0.4). The recovered fractions were then evaporated to complete dryness, affording 1.87 g of the title product (82%).

$^1$H-NMR (CDCl$_3$, δ): 8.55 (dd, 2H, pyridine H6); 7.58 (ddd, 2H, pyridine H4); 7.36 (dd, 2H, pyridine H3); 7.10 (ddd, 2H, pyridine H5); 6.79–7.03 (m, 4H, methoxyphenyl CHs); 4.37 (t, 1H, CH); 3.84 (s, 3H, OCH$_3$); 2.95–3.12 (m, 4H, piperazine protons); 2.55–2.73 (m, 4H, piperazine protons); 2.30–2.55 (m, 4H, CCH$_2$CH$_2$N).

EXAMPLE 9

1-[3-phenyl-3-(2-pyridyl)propyl]-4-(2-methoxyphenyl)piperazine and

EXAMPLE 10

1-[3-aminocarbonyl-3-phenyl-3-(2-pyridyl)propyl]-4-(2-methoxyphenyl)piperazine

A mixture of 1.26 g of compound of Example 7 and 6.2 mL of 70% sulphuric acid was stirred for 40 min at 125° C. The obtained reaction mixture was then cooled to room temperature, poured cautiously into 60 g of ice, diluted with water, alkalinized with 35% sodium hydroxide, and extracted with ethyl acetate (2×60 mL). The combined organic phases were then washed with water and dried on anhydrous sodium sulphate, followed by evaporation to dryness under vacuum. The obtained crude was then purifed by flash chromatography (ethyl acetate-petroleum ether-2.7 N solution of ammonia in methanol gradient from 5:5:0.5 to 8:2:0.5). Subsequent evaporation to dryness in vacuo of the less polar fractions afforded 0.25 g of the compound of Example 9.

$^1$H-NMR (CDCl$_3$, δ): 8.59 (dd, 1H, pyridine H6); 7.54 (ddd, 1H, pyridine H4); 7.08–7.41 (m, 7H, pyridine H3, 5, phenyl CHs); 6.82–7.07 (m, 4H, methoxyphenyl CHs); 4.18 (t, 1H, C$\underline{H}$CH$_2$); 3.85 (s, 3H, OCH$_3$); 3.00–3.15 (m, 4H, piperazine protons); 2.25–2.73 (m, 8H, piperazine protons and CH$_2$CH$_2$).

The evaporation of the more polar fractions, afforded 0.78 g of the product of Example 10 as an oil. This was crystallized from acetonitrile, yielding, after filtration, 0.35 g of a solid melting at 156–164° C.

$^1$H-NMR (CDCl$_3$, δ,): 9.20–9.40 (br, 1H, CONH$_2$); 8.55 (dd, 1H, pyridine H6); 7.60 (dd, 1H, pyridine H4); 7.10–7.35 (m, 7H, pyridine H3, 5, phenyl CHs); 6.80–7.05 (m, 4H, methoxyphenyl CHs); 5.60–5.75 (br, 1H, CONH$_2$); 3.83 (s, 3H, OCH$_3$); 2.15–3.15 (m, 12H, piperazine protons and CH$_2$CH$_2$).

EXAMPLE 11

1-[N-(2-nitrophenyl)-N-(2-pyridyl)-2-aminoethyl]-4-(2-methoxyphenyl)-piperazine

A mixture of 0.43 g of 1-[N-(2-nitrophenyl)-2-aminoethyl]-4-(2-methoxyphenyl)piperazine (prepared as described in U.S. Pat. No. 3,472,854), 0.19 g of 2-bromopyridine, 0.17 g of anhydrous potassium carbonate and 0.01 g of powdered copper was heated to 100° C., and maintained at that temperature for 3 h, followed by the addition of another 0.138 g of 2-bromopyridine, and the heating of the mixture to 160° C. for 24 h. After cooling the mixture to room temperature and extraction with ethyl acetate (2×20 mL), the combined organic phases were then washed with water, dried on sodium sulphate, and evaporated to dryness in vacuo. The obtained crude was next purified by flash chromatography (ethyl acetate-petroleum ether 7:3). The recovered fractions, after evaporation to dryness, afforded 0.25 g of the compound of Example 11 (52%).

$^1$H-NMR (CDCl$_3$, δ): 8.12 (dd, 1H, pyridine H6); 7.98 (dd, 1H, nitrophenyl H3); 7.52–7.70 (m, 2H, aromatics); 7.30–7.50 (m, 2H, aromatics); 6.79–7.03 (m, 4H, methoxyphenyl CHs); 6.65 (dd, 1H, pyridine H5); 6.33 (dd, 1H, pyridine H3); 4.08 (t, 2H, CH$_2$NPy); 3.84 (s, 3H, OCH$_3$); 2.90–3.05 (m, 4H, piperazine protons); 2.80 (t, 2H, CH$_2$CH$_2$NPy); 2.60–2.75 (m, 4H, piperazine protons).

EXAMPLE 12

1-[3-cyano-3-(2-nitrophenyl)-3-phenylpropyl]-4-(2-methoxyphenyl)piperazine a) 1-(3-cyano-3-phenylpropyl)-4-(2-methoxyphenyl) piperazine (Compound 12A):

This product was synthesized here by of the method described above, (in Example 6), with the replacement of 2,2-bis-(2-pyridyl)acetonitrile with phenylacetonitrile, and substituting toluene for 1,2-dimethoxyethane. The obtained reaction mixture was stirred for 3.5 h at 80° C. The obtained crude was then purified by flash chromatogrpahy (ethyl acetate-petroleum ether 6:4). The recovered fractions were then evaporated to dryness, yielding 0.96 g of the title compound (57.3%).

$^1$H-NMR (CDCl$_3$, δ): 7.35–7.45 (m, 5H, phenyl CHs); 6.79–7.03 (m, 4H, methoxyphenyl CHs); 4.08 (t, 1H, CH); 3.86 (s, 3H, OCH$_3$); 3.05–3.20 (m, 4H, piperazine protons); 2.38–2.70 (m, 6H, piperazine protons, 2H of CH$_2$CH$_2$); 1.95–2.35 (m, 2H, 2H of CH$_2$CH$_2$).

b) 1-[3-cyano-3-(2-nitrophenyl)-3-phenylpropyl]-4-(2-methoxyphenyl)piperazine:

A mixture of 0.24 g of Compound 12A, 0.11 g of 2-chloro-nitrobenzene, 0.5 mL of 50% sodium hydroxide 0.02 g of triethyl benyl ammonium chloride, and 0.5 mL of toluene was stirred for 6 h at 60° C., followed by cooling of the mixture to room temperature, dilution with 20 mL of water, and extraction with ethyl acetate (2×20 mL). The combined organic phases were then washed with water, dried on sodium sulphate, and evaporated to dryness under vacuum. The obtained crude material was purified by flash chromatography (ethyl acetate-petroleum ether 5:5). The recovered fractions were then evaporated to complete dryness, yielding 0.12 g of the compound of Example 12 (36%). This was then dissolved in methylene chloride, evaporated to dryness under vacuum, and desiccated in vacuo (1 mmHg). M.p.61–64° C.

$^1$H-NMR (CDCl$_3$, δ): 8.05 (dd, 1H, nitrophenyl H3); 7.50–7.73 (m, 3H, nitrophenyl H 4, 5, 6); 7.20–7.35 (m, 5H, phenyl CHs); 6.79–7.03 (m, 4H, methoxyphenyl CHs); 3.84 (s, 3H, OCH$_3$); 2.95–3.15 (m, 5H, piperazine protons, CH(H̲)CH$_2$N); 2.35–2.75 (m, 7H, piperazine protons, CHH̲C H$_2$N).

EXAMPLE 13

1-[3-aminocarbonyl-3-(2-nitrophenyl)-3-phenylpropyl]-4-(2-methoxyphenyl)-piperazine This product was obtained by of the method described above, (in Example 8), with the exception that the compound of Example 12, rather than the compound of Example 6, was heated at 125° C. for 105 min. After the usual work-up, the obtained crude was purified by flash chromatography (ethyl acetate-methanol 95:5). The recovered fractions were then evaporated to dryness, affording 0.1 g of the title compound, as an oil (46%).

$^1$H-NMR (CDCl$_3$, δ): 7.75–7.82 (m, 1H, nitrophenyl H3); 7.55–7.80 (m, 1H, CONH$_2$); 7.25–7.50 (m, 7H, phenyl CHs, nitrophenyl H 4, 5); 7.05–7.15 (m, 1H, nitrophenyl H6); 6.79–7.03 (m, 4H, methoxyphenyl CHs); 5.30–5.55 (m, 1H, CONH$_2$); 3.84 (s, 3H, OCH$_3$); 3.00–3.15 (m, 4H, piperazine protons); 2.25–2.95 (m, 8H, piperazine protons, CH$_2$CH$_2$).

EXAMPLE 14

1-[3-hydroxy-3,3-bis-(2-pyridyl)propyl]-4-(2-methoxyphenyl)piperazine

To a solution of 0.17 mL of 2-bromopyridine in 6 mL of tetrahydrofuran, stirred under a nitrogen atmosphere, at a temperature of −50° C., there was added dropwise over a period of 5 min, 0.72 mL of butyl lithium (2.5 M solution, in hexane). After 6 min at −55° C., was added dropwise, over a period of 10 min, a solution of 0.5 g of ethyl 3-[4-(2-methoxyphenyl)-1-piperazinyl] propionate (prepared as described in German Patent DE 2, 555, 290) in 3 mL of anhydrous tetrahydrofuran. Next, after keeping for 1.5 h at −50° C., the reaction was quenched by addition of a saturated ammonium chloride solution. The resultant mixture was then extracted with 2×50 mL ethyl acetate. The combined organic phases were then washed with water, dried on sodium sulphate, and evaporated to dryness in vacuo. The obtained crude was then purified by flash chromatography (ethyl acetate-2.2 N solution of ammonia in methanol; 99:1). Finally, the recovered fractions were evaporated to dryness, yielding 0.11 g of the title compound (15%).

¹H-NMR (CDCl₃, δ): 8.56 (dd, 2H, pyridine H6); 7.79 (dd, 2H, pyridine H4); 7.64 (ddd, 2H, pyridine H3); 7.10 (ddd, 2H, pyridine H5); 6.85–7.03 (m, 4H, methoxyphenyl CHs); 3.84 (s, 3H, OCH₃); 2.95–3.12 (m, 4H, piperazine protons); 2.76 (t, 2H, C(OH)CH₂CH₂); 2.55–2.75 (m, 4H, piperazine protons); 2.50 (t, 2H, C(OH)CH₂CH₂).

EXAMPLE 15

1-[3-cyano-3-(2-nitrophenyl)-3-(2-pyridyl)propyl]-4-(2-methoxyphenyl)piperazine a) 1-[3-cyano-3-(2-pyridyl)propyl]-4-(2-methoxyphenyl)piperazine (Compound 15A):

This product was synthesized here by means of the method described above, (in Example 6), with the replacement of 2,2-bis-(2-pyridyl)acetonitrile with 2-(2-pyridyl)acetonitrile and stirring at reflux for 3.5 h. The obtained crude was then purified by flash chromatogrpahy (ethyl acetate). The recovered fractions were then evaporated to dryness, affording of the title compound (46.3%).

¹H-NMR (CDCl₃,δ): 8.60 (dd, 1H, pyridine H6); 7.75 (ddd, 1H, pyridine H4); 7.45 (dd, 1H, pyridine H3); 7.25 (ddd, 1H, pyridine H5); 6.85–7.05 (m, 4H, methoxyphenyl CHs); 4.25 (dt, 1H, CHCN), 3.85 (s, 3H, OCH₃); 3.05–3.15 (m, 4H, piperazine protons); 2.45–2.75 (m, 6H, piperazine protons and CHCH₂CH₂); 2.15–2.35 (m, 2H, CHCH₂CH₂).

b) 1-[3-cyano-3-(2-nitrophenyl)-3-(2-pyridyl)propyl]-4-(2-methoxyphenyl)piperazine:

A solution of 0.66 g of compound 15A in 5 mL of 1,2-dimethoxyethane, was added dropwise at room temperature to a suspension of 0.09 g of 95% sodium amide in 2.5 mL of 1,2-dimethoxyethane. After 1.5 h, a solution of 0.23 mL of 1-fluoro-2-nitrobenzene in 1 mL of 1,2-dimethoxyetane was added and the mixture was refluxed for 20 h. after cooling to room temperature, the reaction mixture was cautiously poured into 20 mL of water and extracted with ethyl acetate. The organic layer was dried on anhydrous sodium sulphate and evaporated to dryness in vacuo. The obtained residue was purified by flash chromatography (ethyl acetate-petroleum ether 7:3) to afford 0.2 g (23%) of the compound of Example 15.

¹H-NMR (CDCl₃, δ): 8.50 (dd, 1H, pyridine H6); 8.00 (ddd, 1H, nitrophenyl H3); 7.65–7.70 (m, 3H, pyridine H4 and 2 CHs of nitrophenyl); 7.50–7.60 (m, 3H, pyridine H3 and 1 CH of nitrophenyl); 7.24 (ddd, 1H, pyridine H5); 6.80–7.05 (m, 4H, methoxyphenyl CHs); 3.84 (s, 3H, OCH₃); 2.90–3.11 (m, 6H, piperazine protons and CCH₂CH₂); 2.40–2.65 (m, 6H, piperazine protons and CHCH₂CH₂).

EXAMPLE 16

1-(4-1H-indolyl)-4-[3,3-bis-(2-pyridyl)propyl]piperazine a) 3,3-bis-(2-pyridyl)propionaldehyde dimethyl acetal (Compound 16A):

This product was prepared as described above, (in Example 5), with the exception that bis-(2-pyridyl)amine was replaced by bis-(2-pyridyl)methane (prepared as described in Heterocycles 1995, 40, 757–776) and substituting 1-(2-chloroethyl)-4-(2-methoxyphenyl)piperazine with 2-bromoacetaldehyde dimethyl acetal. After 12.5 h at reflux the reaction mixture was worked-up as described above. The crude residue was purified by flash chromatography (ethyl acetate-petroleum ether-2.2 N methanolic ammonia 6:4:0.6) affording the title product (77%).

¹H-NMR (CDCl₃, δ): 8.53 (dd, 2H, pyridine H6); 7.57 (ddd, 2H, pyridine H4); 7.33 (dd, 2H, pyridine H3); 7.10 (ddd, 2H, pyridine H5); 4.45 (t, 1H, CH(OCH₃)₂); 4.20 (t, 1H, CHC); 3.27 (s, 6H, OCH₃); 2.57 (dd, 2H, CH₂).

b) 3,3-bis-(2-pyridyl)propionaldehyde (Compound 16B)

A solution of 1.86 g of Compound 16A and 0.08 g of 1,4-dihydroquinone in 36 mL of 2 N HCl was stirred at 80° C. for 15 min, cooled to 0° C., diluted with 50 mL of dichloromethane and neutralized with 20% aq. sodium carbonate (pH=7–8). The organic layer was dried on sodium sulphate and evaporated to dryness affording 1.15 g of crude title compound as a grey glassy solid, which was used in the next step without any further purification.

c) 1-(4-1H-indolyl)-4-[3,3-bis-(2-pyridyl)propyl]piperazine

A mixture of 1.15 g of Compound 16B, 1.2 g of 1-(4-indolyl)piperazine (prepared as described in EP 138,280), 1.24 mL of acetic acid, 1.71 g of sodium triacetoxyborohydride and 85 mL of 1,2-dichloroethane was stirred at room temperature for 24 h. Afterwards it was diluted with water and alkalinized with sodium carbonate. The organic layer was dried on sodium sulphate and evaporated to dryness affording 1.53 g of crude, which was purified by flash chromatography (ethyl acetate-2.2 N methanolic ammonia, gradient from 9.4:0.6 to 9.2:0.8) affording 0.28 g (13%) of the title product as an oil.

¹H-NMR (CDCl₃, δ): 8.55 (dd, 2H, pyridine H6); 8.25 (bs, 1H, NH), 7.52 (ddd, 2H, pyridine H4); 7.38 (dd, 2H, pyridine H3); 7.02–7.17 (m, 5H, pyridine H5, indole H2, 6, 7); 6.50–6.60 (m, 2H, indole H3, 5); 4.40 (t, 1H, CH); 3.15–3.30 (m, 4H, piperazine protons); 2.60–2.75 (m, 4H, piperazine protons); 2.35–2.60 (m, 4H, CCH₂CH₂N).

EXAMPLE 17

1-[3-aminocarbonyl-3-(2-nitrophenyl)-3-(2-pyridyl)propyl]-4-(2-methoxyphenyl)-piperazine This product was prepared as described above in Example 10, with the exception that the compound of Example 7 was replaced by the compound of Example 15 and the reaction mixture was stirred at 140° C. for 2.5 h. The obtained reaction mixture was then cooled to room temperature, diluted with water, alkalinized with 35% sodium hydroxide and extracted with methylene chloride. The organic layer was washed with water and dried on anhydrous sodium sulphate, followed by evaporation to dryness under vacuum. The obtained crude was then purifed by flash chromatography (ethyl acetate-methanol 9.5:0.5). Subsequent evaporation to dryness in vacuo of the less polar fractions afforded the title compound (37%) as a solid melting at 63–72° C.

¹H-NMR (CDCl₃, δ): 8.50 (dd, 1H, pyridine H6); 8.00 (ddd, 1H, nitrophenyl H3); 7.65–7.70 (m, 3H, pyridine H4 and 2 CHs of nitrophenyl); 7.50–7.60 (m, 3H, pyridine H3 and 1 CH of nitrophenyl); 7.24 (ddd, 1H, pyridine H5); 6.80–7.05 (m, 4H, methoxyphenyl CHs); 3.84 (s, 3H, OCH₃); 2.90–3.11 (m, 6H, piperazine protons and CCH₂CH₂); 2.40–2.65 (m, 6H, piperazine protors and CCH₂CH₂).

EXAMPLE 18

Effects on Volume-Induced Rhythmic Bladder Voiding Contractions in Anaesthetized Rats A. Methods:

Female Sprague Dawley rats weighing 225–275 g (Crl:CDo BR, Charles River Italia) were used. The animals were housed with free access to food and water and were maintained on a forced 12 h alternating light-dark cycle at 22–24° C. for at least one week, except during the experiment. The activity on the rhythmic bladder voiding contractions was evaluated according to the method of Dray (J. Pharmacol. Methods, 13:157, 1985), with some modifications as in Guarneri (Pharmacol. Res., 27:173, 1993). Briefly, rats were anesthetized by subcutaneous injection of 1.25 g/kg (5 ml/kg) urethane, after which the urinary bladder was catheterized via the urethra using PE 50 polyethylene tubing filled with physiological saline. The catheter was tied in place with a ligature around the external urethral orifice and was connected with conventional pressure transducers (Statham P23 ID/P23 XL). The intravesical pressure was displayed continuously on a chart recorder (Battaglia Rangoni KV 135 with DCl/TI amplifier). The bladder was then filled via the recording catheter by incremental volumes of warm (37° C.) saline until reflex bladder voiding contractions occurred (usually 0.8–1.5 ml). For intravenous (i.v.) injection of bioactive compounds, PE 50 polyethylene tubing filled with physiological saline was inserted into the jugular vein.

From the cystometrogram, the number of contractions recorded 15 min before (basal values) and after treatment, as well as the mean amplitude of these contractions (mean height of the peaks in mm Hg) was evaluated.

Since most compounds produced an effect that was relatively rapid in onset and led to a complete cessation of bladder contractions, bioactivity was conveniently estimated by measuring the duration of bladder quiescence (i.e., the duration of time during which no contractions occurred). Moreover, the number of animals tested showing a reduction in the number of contractions >30% of that observed in the basal period, was recorded. To compare the potency of the tested compounds for inhibiting bladder voiding contractions, equieffective doses which resulted in a disappearance time of 10 minutes ($ED_{10min}$) were computed by means of least square linear regression analysis. Also computed in this manner were extrapolated doses which induced a reduction of the number of contractions of greater than 30% in 50% of treated rats ($ED_{50}$, frequency) by the method of Bliss (Bliss C. I., Quart. J. Pharm. Pharmacol. 11, 192–216, 1938). After the suppressive effects of drug injection wore off, the height of the contractile peaks was compared with the height of the peaks previously recorded after the control intravenous administration of vehicle. The potency of the tested compounds ($ED_{50}$ value, the extrapolated doses inducing a 30% reduction of amplitude of the contractions in 50% of treated rats) was evaluated on a quantal basis by the method of Bliss (Bliss C. I., Quart. J. Pharm. Pharmacol. 11, 192–216, 1938).

B. Results

The rapid distension of the urinary bladder in urethane-anesthetized rats produced a series of rhythmic bladder voiding contractions whose characteristics have been described and are well-known in the art (Maggi et al., Brain Res., 380:83, 1986; Maggi, et al., J. Pharmacol. Exp. Ther., 230:500, 1984). The frequency of these contractions is related to the sensory afferent arm of reflex micturition and to the integrity of the micturition center, while their amplitude is a property of the efferent arm of the reflex. In this model system, compounds that act mainly on the CNS (such as morphine) cause a block in voiding contraction, whereas drugs that act at the level of the detrusor muscle, such as oxybutynin, lower the amplitude of the bladder contractions.

The results obtained after administration of prior art compounds and compounds of the invention are shown in Table 1.

TABLE 1

Effects on rhythmic bladder voiding contractions after intravenous administration. Data represent the $ED_{10min}$ values (the extrapolated dose inducing 10 min of disappearance of the contractions); the $ED_{50}$ values (the extrapolated doses inducing a reduction of the number of contractions >30% in 50% of treated rats) (frequency), and the $ED_{50}$ values (the extrapolated doses inducing 30% reduction of amplitude of the contractions in 50% of treated rats) (amplitude).

| Compound | $ED_{10min}$ | $ED_{50}$ (frequency) µg/kg | $ED_{50}$ (amplitude) µg/kg |
|---|---|---|---|
| Ex. 5 | 523 | 77 | n.a. |
| Ex. 6 | 225 | 93 | n.a. |
| Ex. 7 | 78 | 18 | n.a. |
| Ex. 8 | 74 | 2.5 | n.a. |
| Ex. 9 | 77 | 25 | n.a. |
| Ex. 10 | 228 | 180 | n.a. |
| Ex. 11 | 162 | 24 | n.a. |
| Ex. 13 | — | 84 | n.a. |
| Ex. 14 | 127 | 36 | n.a. |
| Flavoxate | >10000 | 2648 | n.a. |
| Oxybutynin | 7770 | 10000 | 240 |
| Imipramine | >6000 | 4930 | 2930 | n.a. = not active; no significant reduction of the height of peaks

All the compounds of the present invention that were tested were markedly more potent than flavoxate, oxybutynin and imipramine in inhibiting voiding contractions, as illustrated by the $ED_{10min}$ and $ED_{50}$ values obtained. In contrast to oxybutynin, and like flavoxate and imipramine, the compounds of the invention did not affect the amplitude of the contractions, indicating no impairment of bladder contractility.

EXAMPLE 19

Radioreceptor Binding to 5-$HT_{1A}$ and Other Different Neurotransmitter Binding Sites A. Methods:

Recombinant Human 5$HT_{1A}$ Receptors:

Genomic clone G-21 coding for the human 5-$HT_{1A}$ serotonergic receptor is stably transfected in a human cell line (HeLa). HeLa cells were grown as monolayers in Dulbecco's modified Eagle's medium (DMEM), supplemented with 10% fetal calf serum and gentamicin (100 mg/ml), 5% $CO_2$ at 37° C. Cells were detached from the growth flask at 95% confluence by a cell scraper and were lysed in ice-cold 5 mM Tris and 5 mM EDTA buffer (pH 7.4). Homogenates were centrifuged at 40000×g×20 min and pellets were resuspended in a small volume of ice-cold 5 mM Tris and 5 mM EDTA buffer (pH 7.4) and immediately frozen and stored at −70° C. until use. On the day of experiment, cell membranes were resuspended in binding buffer: 50 mM Tris HCl (pH 7.4), 2.5 mM MgCl$_2$, 10 μM pargyline (Fargin et al., Nature 335, 358–360, 1988). Membranes were incubated in a final volume of 1 ml for 30 min at 30° C. with 0.2–1 nM [$^3$H]8-OH-DPAT, in absence or presence of competing drugs; non-specific binding was determined in the presence of 10 μM 5-HT. The incubation was stopped by addition of ice-cold Tris-HCl buffer and rapid filtration through 0.2% polyethyleneimine-pretreated Whatman GF/B or Schleieher & Schuell GF52 filters.

Native 5-HT$_{2A}$ Serotonergic Receptors (from Animal Tissues)

Binding studies on native 5-HT$_{2A}$ serotonergic receptors (Craig A. and Kenneth J., Life Sci. 38, 117–127, 1986) were carried out in membranes of rat cerebral cortex. Male Sprague Dawley rats (200–300 g, S D Harlan/Nossan, Italy) were killed by cervical dislocation and cerebral cortexes were excised and immediately frozen in liquid nitrogen and stored at −70° C. until use. Tissues were homogenized (2×20 sec) in 50 volumes of cold 50 mM Tris-HCl buffer pH 7.4, using a Polytron homogenizer (speed 7). Homogenates were centrifuged at 49000×g for 10 min, resuspended in 50 volumes of the same buffer, incubated at 37° C. for 15 min and centrifuged and resuspended twice more. The final pellets were suspended in 100 volumes of 50 mM Tris-HCl buffer pH 7.7. Membranes were incubated in a final volume of 1 ml for 20 min at 37° C. with 0.7–1.3 nM [$^3$H]ketanserin (5-HT$_{2A}$ receptors), in absence or presence of competing drugs. Non-specific binding was determined in the presence of 2 μM ketanserin. The incubation was stopped by addition of ice-cold 50 mM Tris-HCl buffer and rapid filtration through 0.2% polyethyleneimine pretreated Whatman GF/B or Schleicher & Schuell GF52 filters. The filters are then washed with ice-cold buffer and the radioactivity retained on the filters was counted by liquid scintillation spectrometry.

Native (Animal Tissues) α$_1$ Adrenergic Receptors

Binding studies on native α$_1$ adrenergic receptors were carried out in membranes of rat cerebral cortex. Male Sprague Dawley rats (200–300 g, Charles River, Italy) were killed by cervical dislocation and cerebral cortexes were dissected and immediately frozen and stored at −70° C. until use. Tissue was homogenized (2×20 sec) in 50 volumes of cold 50 mM Tris-HCl buffer pH 7.4, using a Polytron homogenizer (speed 7). Homogenates were centrifuged at 48000×g for 10 min, resuspended in 50 volumes of the same buffer, incubated at 37° C. for 15 min and centrifuged and resuspended twice more. The final pellets were suspended in 100 volumes of 50 mM Tris-HCl buffer pH 7.4, containing 10 μM pargyline and 0.1% ascorbic acid. Membranes were incubated in a final volume of 1 ml for 30 min at 25° C. with 0.1–0.5 nM [$^3$H]prazosin, in the absence or presence of competing drugs; non-specific binding was determined in the presence of 10 μM phentolamine.

The incubation was stopped by addition of ice-cold 50 mM Tris-HCl buffer and rapid filtration through 0.2% polyethyleneimine-pretreated Whatman GF/B or Schleicher & Schuell GF52 filters. The filters were then washed with ice-cold buffer and the radioactivity retained on the filters counted by liquid scintillation spectrometry.

B. Results:

The inhibition of specific binding of the radioligands by the tested drugs was analyzed to estimate the IC$_{50}$ value by using the non-linear curve-fitting program Allfit (De Lean et al., Am. J. Physiol. 235, E97-E102, 1978). The IC$_{50}$ value is converted to an affinity constant (Ki) by the equation of Cheng & Prusoff (Cheng, Y. C.; Prusoff, W. H. Biochem. Pharmacol. 22, 3099–3108, 1973).

The results are shown in Table 2. These results indicate that the compounds of the present invention have a high affinity for the 5-HT$_{1A}$ receptor, and are selective for this receptor relative to their affinity for the 5-HT$_{2A}$ receptor and α$_1$-adrenoceptors.

TABLE 2

Binding affinity for the 5-HT$_{1A}$ receptor and other neurotransmitter binding sites
Data are expressed as Ki (nM).

| Compound | 5-HT$_{1A}$ | 5-HT$_{2A}$ | α$_1$ |
|---|---|---|---|
| Ex. 1 | 3.9 | 320 | 145 |
| Ex. 2 | 0.6 | 159 | 208 |
| Ex. 6 | 13.3 | — | 1246 |
| Ex. 7 | 7.7 | 140 | 396 |
| Ex. 8 | 3.97 | 320 | 191 |
| Ex. 9 | 0.62 | 1023 | 268 |
| Ex. 10 | 19.3 | 683 | 1322 |
| Ex. 11 | 6.74 | — | 62.5 |
| Ex. 12 | 1.45 | 790 | 226 |
| Ex. 13 | 2.30 | — | 365 |
| Ex. 14 | 0.34 | >1000 | 114 |
| Ex. 17 | 5.18 | — | 307 |

What is claimed is:

1. A compound of the formula

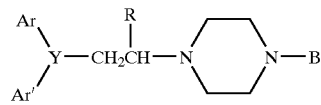

wherein
each of Ar and Ar' is independently selected from the group consisting of phenyl and pyridyl, each optionally substituted by one or more members selected from the group consisting of alkyl, alkoxy, cyano, nitro, amino, alkylsulfonylamino, and alkylamino;
Y is a member selected from the group consisting of nitrogen atom, CH, C—OH, and C—CN;
R is a hydrogen atom or a lower alkyl group;
B is selected from the group consisting of (i) phenyl, (ii) naphthyl, (iii) benzodioxanyl, and (iv) indolyl; wherein a phenyl ring of said B is optionally substituted with one or more substituents selected from the group consisting of hydrogen atom, alkyl, alkoxy, halogen, cyano, nitro, amino, alkylsulfonylamino and alkylamino; with the provisos that
  1) when B is methoxyphenyl and Y is C—CN then Ar and Ar' are not simultaneously unsubstituted phenyl; alkylphanyl;
  2) when Y is CH, Ar and Ar' cannot both be optionally substituted pyridyl;
  3) when Y is CH and one of Ar and Ar' is optionally substituted phenyl, the other of Ar' and Ar cannot be optionally substituted pyridyl; and
  4) when Y is CH or a nitrogen atom and each of Ar and Ar' are optionally substituted phenyl wherein said substitution is methyl, then B is selected from the group consisting of (i) phenyl, (ii) naphthyl, (iii) benzodioxanyl, and (iv) indolyl; wherein a phenyl rind of said B is optionally substituted with one or more substituents selected from the group consisting of alkoxy, halogen, cyano, nitro, amino, alkylsulfonylamino and alkylamino groups; and enantiomers, diastereomers, N-oxides crystalline forms, hydrates and pharmaceutically acceptable salts thereof.

2. A compound of claim 1 wherein Y is nitrogen, CH, C—OH, or C—CN.

3. A compound selected from the group consisting of:

1-(3,3-diphenylpropyl)-4-(2-methoxyphenyl)piperazine;

1-(3,3-diphenylpropyl)-4-[5-(2,3-dihydro-1,4-benzodioxinyl)]piperazine;

1-[3,3-bis-(4-nitrophenyl)propyl]-4-(2-methoxyphenyl)piperazine;

1-[3,3-bis-(4-methoxyphenyl)propyl]-4-(2-methoxyphenyl)piperazine;

1-[N-N-bis-(2-pyridyl)-2-aminoethyl]-4-(2-methoxyphenyl)piperazine;

1-[3-aminocarbonyl-3-phenyl-3-(2-pyridyl)propyl]-4-(2-methoxyphenyl)piperazine;

1-[3-cyano-3-(2-nitrophenyl)-3-phenylpropyl]-4-(2-methoxyphenyl)piperazine;

1-[3-aminocarbonyl-3-(2-nitrophenyl)-3-phenylpropyl]-4-(2-methoxyphenyl)piperazine;

1-[3-cyano-3-(2-nitrophenyl)-3-(2-pyridyl)propyl]-4-(2-methoxyphenyl)piperazine;

1-[3-aminocarbonyl-3-(2-nitrophenyl)-3-(2-pyridyl)propyl]-4-(2-methoxyphenyl)-piperazine; and enantiomers, N-oxides, hydrates, and pharmaceutically acceptable salts thereof.

4. A compound selected from the group consisting of:

1-[3-hydroxy-3,3-bis-(2-pyridyl)propyl]-4-(2-methoxyphenyl)piperazine;

1-(4-1H-indolyl)-4-[3,3-bis-(2-pyridyl)propyl]piperazine;

1-[3-cyano-3,3-bis-(2-pyridyl)propyl]-4-(2-methoxyphenyl)piperazine;

1-[3-cyano-3-phenyl-3-(2-pyridyl)propyl]-4-(2-methoxyphenyl)piperazine; and

1-[N-(2-nitrophenyl)-N-(2-pyridyl)-2-aminoethyl]-4-(2-methoxyphenyl)piperazine.

5. A pharmaceutical composition of a compound of claim 1 and a pharmaceutically acceptable diluent or carrier.

6. A pharmaceutical composition of a compound of claim 2 and a pharmaceutically acceptable diluent or carrier.

7. A pharmaceutical composition of a compound of claim 3 and a pharmaceutically acceptable diluent or carrier.

8. The pharmaceutical composition of claim 7 which comprises at least one excipient selected from the group consisting of lubricants, plasticizers, colorants, absorption enhancers, and bactericides.

* * * * *